(12) United States Patent
Andersson et al.

(10) Patent No.: US 7,036,157 B1
(45) Date of Patent: May 2, 2006

(54) METHOD OF PRODUCING A HOOD, AND A HOOD PRODUCED ACCORDING TO THE METHOD

(75) Inventors: Magnus Andersson, Värnamo (SE); Jan Folkesson, Värnamo (SE)

(73) Assignee: Peltor AB, (SE)

( * ) Notice: Subject to any disclaimer, the term of this patent is extended or adjusted under 35 U.S.C. 154(b) by 574 days.

(21) Appl. No.: 10/030,505

(22) PCT Filed: Jun. 15, 2000

(86) PCT No.: PCT/SE00/01248

§ 371 (c)(1),
(2), (4) Date: Jun. 3, 2002

(87) PCT Pub. No.: WO01/03623

PCT Pub. Date: Jan. 18, 2001

(30) Foreign Application Priority Data

Jul. 8, 1999 (SE) .................................. 9902643

(51) Int. Cl.
*A42B 1/06* (2006.01)

(52) U.S. Cl. .............................. 2/209; 2/423; 181/129

(58) Field of Classification Search ................... 2/209, 2/203, 423, 455; 128/864; 181/129; 379/433
See application file for complete search history.

(56) References Cited

U.S. PATENT DOCUMENTS

| | | | |
|---|---|---|---|
| 3,506,980 A * | 4/1970 | Aileo | 2/209 |
| 3,593,341 A * | 7/1971 | Aileo | 2/209 |
| 3,875,592 A | 4/1975 | Aileo | |
| 3,944,018 A * | 3/1976 | Satory | 181/175 |
| 4,471,496 A | 9/1984 | Gardner, Jr. et al. | |
| D298,670 S | 11/1988 | Palmaer | |
| 4,905,322 A * | 3/1990 | Aileo et al. | 2/209 |
| 5,020,163 A * | 6/1991 | Aileo et al. | 2/209 |
| 5,023,955 A | 6/1991 | Murphy, II et al. | |
| 5,138,722 A * | 8/1992 | Urella et al. | 2/209 |
| 5,500,958 A * | 3/1996 | Falco | 2/209 |
| D375,584 S | 11/1996 | Westerdal | |
| D385,665 S | 10/1997 | Westerdal | |
| 5,747,549 A * | 5/1998 | Tsurugai et al. | 521/60 |
| D409,615 S | 5/1999 | Sloan | |
| D410,238 S | 5/1999 | Sloan | |
| 5,920,911 A * | 7/1999 | Cushman | 2/209 |
| D413,413 S | 8/1999 | Dillon et al. | |
| 5,988,313 A | 11/1999 | Hakansson | |
| 6,264,870 B1 | 7/2001 | Hakansson | |

FOREIGN PATENT DOCUMENTS

| | | |
|---|---|---|
| DE | 34 41 120 A1 | 11/1984 |
| DE | 34 41 122 A1 | 11/1984 |
| EP | 0 484 306 A1 | 10/1991 |
| WO | WO 94/24185 | 10/1994 |

\* cited by examiner

*Primary Examiner*—Tejash Patel
(74) *Attorney, Agent, or Firm*—Cantor Colburn LLP

(57) ABSTRACT

The disclosure relates to a method of producing a hood for a hearing protector by injection moulding of plastic material. The hood is injection moulded to a single contiguous piece employing at least two plastic materials possessing different properties in at least one respect. The plastic materials may be both homogeneous and in porous or foamed form. A hood for a hearing protector is produced from plastic by injection moulding. The hood includes at least two portions or layers which are united to one another. The portions or layers consist of plastic materials with different properties in at least one respect.

113 Claims, 2 Drawing Sheets

US 7,036,157 B1

METHOD OF PRODUCING A HOOD, AND A HOOD PRODUCED ACCORDING TO THE METHOD

FIELD OF THE INVENTION

The present invention relates to a method of producing a hood for a hearing protector, the hood being produced by injection moulding of plastic material.

The present invention also relates to a hood for a hearing protector in which the hood is produced from plastic by injection moulding.

DESCRIPTION OF THE RELATED ART

A multiplicity of various acoustic hoods are previously known in the art for use in hearing protectors. Such hoods may be simple and consist of a cup-shaped shell injection moulded from plastic which is secured in one end of an arc which is placed over the head of the wearer and which has a similar hood at its opposite end. The hoods are dimensioned to enclose the wearer's ears.

A hood consisting exclusively of a shell is, despite quite complicated configuration, readily subjected to vibrations and oscillations, throughout the entirety of the hood or only locally in it, which implies that the sound-suppression or sound insulation which the hood achieves-will be unpredictable and uneven within various frequency ranges.

In order to obviate the above-mentioned problem, various inlays of different sound-absorbing materials have been placed interiorly in the hood. Such solutions also suffer from similar drawbacks.

EP 484 306 discloses a hearing protector in which the hoods have a hard outer shell, inside this a casing of compressed foamed plastic, and inside this casing a further hard hood, which realises compression of the foamed layer lying outside. Interiorly in the inner hood, a sound-absorbent material is then placed.

Such a construction functions considerably better than the above-described construction consisting merely of a shell which is provided interiorly with a sound-absorbent. However, the construction is not optimal, either as regards rational production or sound-suppression/sound-insulation.

Similar constructions are also known from USPS 2 684 067, DE 3 441 120, DE 3 441 122, and others.

For a hood to be as favourable as possible in a hearing protector, the material in the hood should be "as dead as possible" so that it has a very slight ability to be excited into oscillation movements both as an entity and also locally.

SUMMARY OF THE INVENTION

The present invention provides a method of manufacturing a hood which obviates the drawbacks inherent in hoods according to prior art technology, and in particular improves the sound-suppression capability of the hood. The present invention further provides extremely rational production of hoods, at the same time as these can be given an extremely aesthetically attractive appearance.

The present invention also obviates the drawbacks inherent in priori art designs and constructions, and in particular improves the sound-suppression capability of the hood. Finally, the present invention provides a the hood such that it may be manufactured economically and rationally in large series and that it may be given an aesthetically attractive exterior.

More specifically, the invention provides a hood that is injection moulded to one single continuous piece using plastic materials with different properties in at least one respect.

As regards the hood, the objects of the present invention will be attained if the hood is characterised in that it includes at least two mutually contiguous portions or layers which consist of plastic material with different properties in at least one respect.

By injection moulding of a hood where different portions are included in the hood, and where the injection moulded plastic material or materials have different properties in at least one respect, a hood will be realised which suffers from considerably less of a risk of being subjected to resonance oscillations both locally and for the hood as an entity. The hood will have improved sound-suppression capability.

Further, the possibility is afforded of extremely rational manufacture.

BRIEF DESCRIPTION OF THE DRAWINGS

The present invention will now be described in greater detail hereinbelow, with particular reference to the accompanying Drawings. In the accompanying Drawings.

DETAILED DESCRIPTION OF THE INVENTION

The basic concept behind the present invention is that there should be included, in one and the same hearing protector hood, at least two portions where the material in each portion differs in one way or another as regards oscillation from the material in the other portion or in the remaining portions. Differences which will be topical for consideration here are differences in density, differences in hardness, differences in modulus of elasticity, differences in structure, for example differences between homogeneous and porous plastic materials, differences between plastic materials with open or closed foamed structure, differences between plastic materials with and without different types of fillers, etc. As examples of usable plastics, mention might be made of ABS plastic, polypropylene, polyethylene and polycarbon plastics, TPE, etc.

The concept which lies behind the present invention takes as its point of departure the fact that a sound wave, i.e. a mechanical oscillation movement, which propagates in a body will at least partly be reflected and refracted when it impinges on an interface between materials with different properties. The reflected and refracted parts of the sound wave will interfere with each other and with the original sound wave, with a diffusion and attenuation of the sound wave as a result. This phenomenon becomes more manifest the higher the frequency the sound wave has.

If one considers a body, e.g. a hood included in a hearing protector, its oscillation properties are determined by material properties, configuration and dimensions. Different materials oscillate at different frequencies if the remaining properties remain constant. If two bodies which oscillate at different frequencies (e.g. depending upon different material properties in the bodies) are mechanically interconnected, the different oscillations will inhibit one another, whereby resonances are obstructed or reduced.

Figure 1:
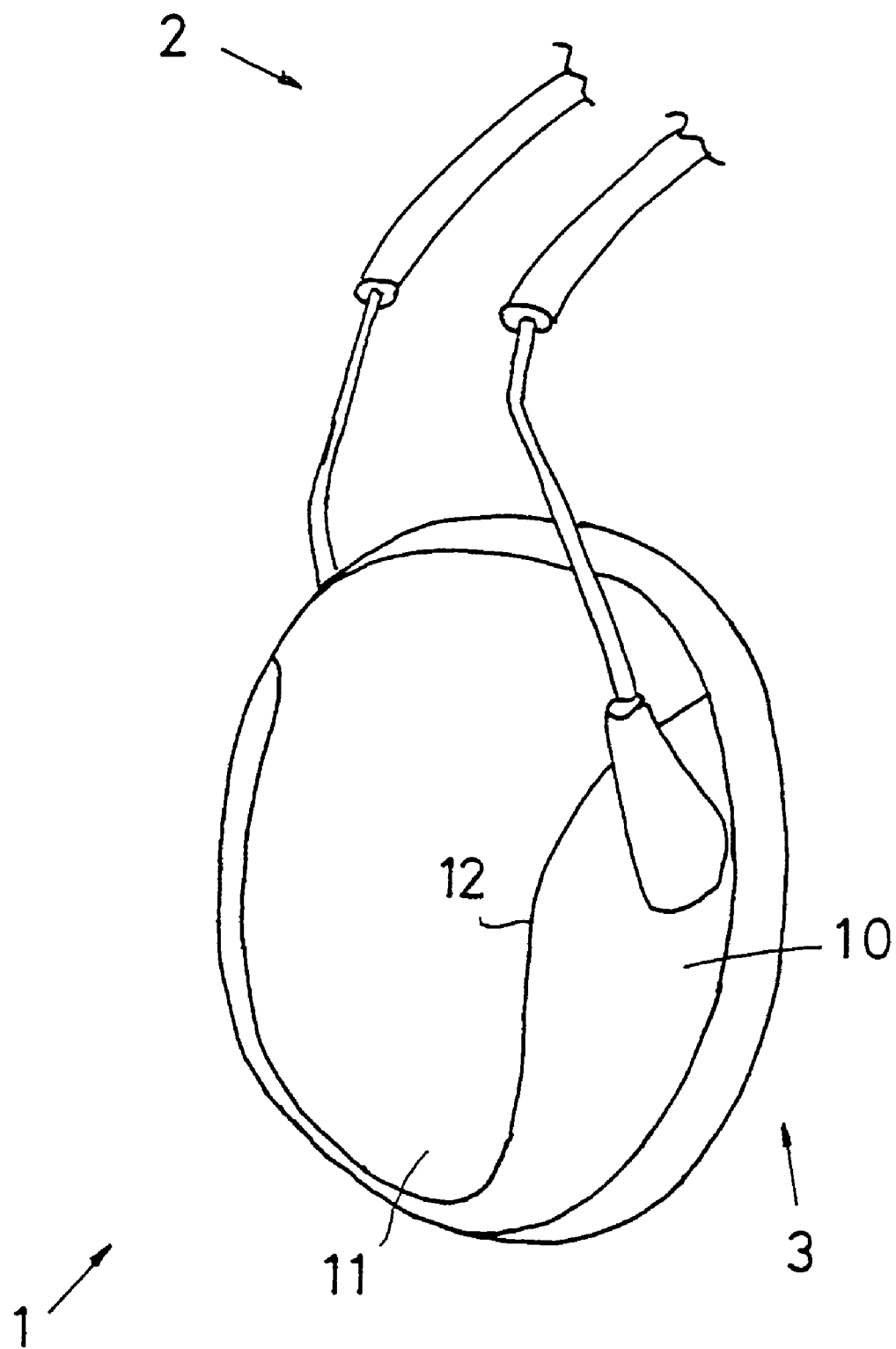
FIG. 1 is a perspective view of a part of a hearing protector employing a hood according to the present invention.

In FIG. 1, reference numeral 1 relates to a hood included in a hearing protector, the hood being pivotally secured in a stirrup 2 which is intended to extend over the head of the wearer of the hearing protector. On the side of the hood 1 facing towards the wearer's head, there is provided an abutment ring 3 which is produced from soft, resilient and yieldable material so that it may form itself according to the head of the person wearing the hearing protector, and thereby realise a seal between the interior of the hood, round the ear of the wearer and the ambient surroundings.

When the word "hood" is employed below and in the appended claims, this refers exclusively to the hood proper without loosely inserted damping material or other equipment and also without the above-mentioned abutment ring.

Figure 2:
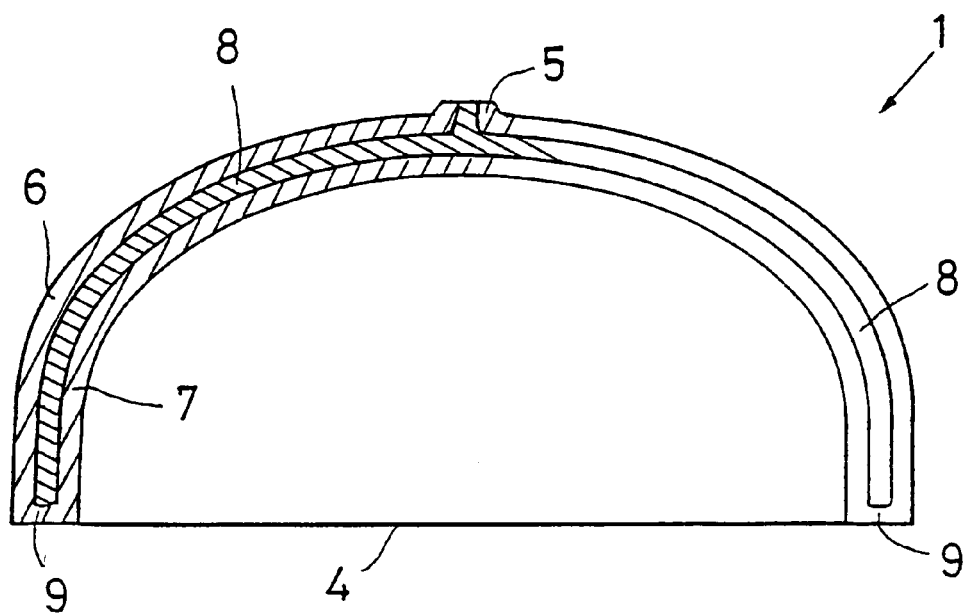
FIG. 2 is a cross section through a first embodiment of a hood according to the present invention.

In the embodiment according to FIG. 2, the hood 1 is produced by injection moulding in accordance with the sandwich method. The hood 1 has a peripheral edge 4 facing towards the wearer's head and along which the above-mentioned-abutment ring 3 is secured.

On its outside, the hood 1 has a sprue 5 via which molten plastic material is injected in under high pressure into the mould in which the hood 1 is produced. According to the sandwich method, a first plastic material which is to form the outer casing 6 of the hood and its inner casing 7 is injected in first. When injection of this first plastic material is completed, the injection continues with a second plastic material which is injected interiorly in the material which formed the outer casing and the inner casing. The first and second plastic materials have different material properties in at least one respect, such as density, hardness, etc. The second plastic material forms an intermediate layer 8 between the outer casing 6 and the inner casing 7. It should be observed that the outer casing 6 and the inner casing 7 have a connecting bridge 9 along the peripheral edge 4 of the hood 1. As a result, the material in the intermediate layer 8 will in principle be totally enclosed between the outer casing and the inner casing, possibly apart from the region at the sprue 5.

On injection moulding according to the sandwich method, the plastic material for the outer casing and the inner casing is fed to the moulding tool via a first feeder screw included in the injection moulding machine. A second feeder screw is employed for injecting the second material for the intermediate layer 8, in which event the tool may either have two separate inlets, one for each screw, or the tool may also be switched from a position for injection via the first screw to a position for injection via the second screw.

In the embodiment according to FIG. 1, the hood 1 has an outer, peripheral portion 10 which extends along the periphery of the hood apart from in its upper region. The bottom of the hood, i.e. substantially its central region, and its upper region are formed from a central portion 11 which is discrete from the outer portion 10 via a separation line 12 which, in practice, is only visual since the material in the outer portion 10 and the central portion 11 in principle form a single, contiguous piece where the different portions have materials with different properties.

In one variation of the embodiment according to FIG. 1, the outer portion 10 has a through-going material thickness such that the hood 1 has the same material externally and internally within the region which is defined by the outer portion 10. The corresponding feature naturally applies to the central portion 11. In another variation of the embodiment according to FIG. 1, the material within the outer portion 10 is double, with an outer layer which has a free surface on the outside of the hood, and an inner layer whose material differs from the material in the outer layer. The corresponding applies to the central portion 11, but however the materials in the outer and inner layers have been reversed, so that the material in the outer layer of the outer portion lies on the inside of the central portion 11, while the material in the outer layer within the central portion 11 lies on the inside of the outer layer in the outer portion 10. In the region of the separation line 12, the layers have mutually corresponding apertures and bridges, which will be illustrated more clearly with reference to FIG. 3.

Figure 3:
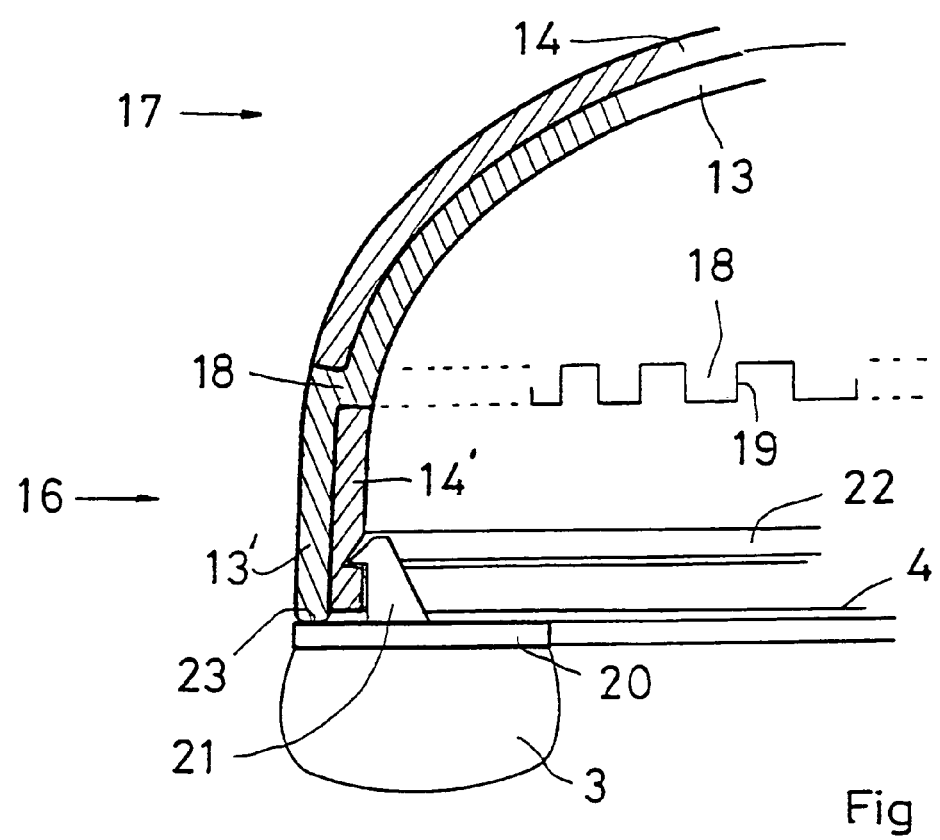
FIG. 3 is a partial cross sectional, on a larger scale, of a second embodiment of a hood according to the present invention.

FIG. 3 shows a duplex layer construction where the division between the layers may have any optionally formed separation lines which can define considerably more different regions than applies in FIG. 1, where only two different regions are shown.

In the embodiment according to FIG. 3, the shell 1 has, in its upper region in the Figure, a soft inner layer 13 and a hard outer layer 14. The two layers 13 and 14 are united to one another in a union interface where the materials have been caused to adhere powerfully to one another, possibly by fusion, during the injection moulding cycle proper. In the lower region of the embodiment according to FIG. 3, the soft material is outermost and forms an external band 13' along the peripheral edge 4 of the hood 1. On the inside of this external band 13', the hard material is located and there forms an inner band 14'.

The transition region between the edge area 16 of the hood 1 and its cupola area 17 includes alternatingly disposed bridges 18 and complementary apertures 19 accommodating the bridges 19.

As will be apparent from FIG. 1, an abutment ring 3 extends along the peripheral edge 4 of the hood 1. This has a carrier ring 20 with catches 21 or a circumferential ring for snapping into a groove 22 in the inside of the inner, hard band 14'. For the satisfactory function of the hearing protector, it is of vital importance that a good seal is obtained, on the one hand, between the interior of the hood 1 and the abutment ring 3 and, on the other hand, between the abutment ring 3 and the head of the wearer of the hearing protector. In the embodiment illustrated in FIG. 3, the outer, soft band 13' has been given the form of a seal 23 which abuts elastically compressed against the upper side of the carrier ring 20.

The division between the portions 10 and 11 of the hood 1 shown in FIG. 1 has been made merely for purposes of exemplification. Aesthetic considerations may be made in this design, without appreciably affecting the acoustic properties of the hood. On the other hand, it might possibly be expected that a division into more than two different contiguous portions may have a favourable effect on the acoustic properties of the hood.

What is claimed is:

1. A method of producing a hood for a hearing protector, comprising: injection molding of plastic material into a single contiguous piece employing plastic materials with different properties in at least one respect wherein said single contiguous piece includes at least two contiguous portions, the hood having an outer surface and an inner surface, said at least two contiguous portions being visible on said outer surface, and wherein one of said at least two contiguous portions comprises a central portion and another of said at least two contiguous portions at least partially surrounds said central portion.

2. The method as claimed in claim 1, wherein the plastic materials are employed in both homogeneous and in porous or foamed form.

3. The method as claimed in claim 1, wherein at least two different plastic materials are employed.

4. The method as claimed in claim 3, wherein plastic materials of different densities are employed.

5. The method as claimed in claim 3, wherein plastic materials of different hardnesses are employed.

6. The method as claimed in claim 3, wherein plastic materials with different modulus of elasticity are employed.

7. A hood for a hearing protector produced from plastic by injection molding, comprising:
at least two mutually contiguous portions which comprise plastic materials with different properties in at least one respect wherein the hood has an outer surface and an inner surface, said at least two contiguous portions being visible on said outer surface, a separation line separating said at least two contiguous portions, and wherein one of said at least two contiguous portions comprises a central portion and another of said at least two contiguous portions at least partially surrounds said central portion.

8. The hood as claimed in claim 7, wherein at least one portion comprises a different plastic material than another portion.

9. The hood as claimed in claim 7, wherein a portion is disposed along a peripheral edge of the hood, is produced from a soft and elastic material, and is designed for sealing against an abutment ring which is disposed along the peripheral edge of the hood and designed to abut against a head of a wearer of the hearing protector in which the hood is included.

10. The method as claimed in claim 1 wherein one of said at least two contiguous portions comprises a softer plastic than the other of said contiguous portions.

11. The method as claimed in claim 1 including an abutment ring attached to said hood.

12. The hood as claimed in claim 7 wherein one of said at least two contiguous portions comprises a softer plastic than the other of said contiguous portions.

13. The hood as claimed in claim 7 including an abutment ring attached to said hood.

14. A hood for a hearing protector comprising:
at least two mutually contiguous portions which comprise plastic materials with different properties in at least one respect; and
wherein the hood has an outer surface and an inner surface, said at least two contiguous portions being visible on said outer surface, a separation line separating said at least two contiguous portions, and wherein one of said at least two contiguous portions comprises a central portion and another of said at least two contiguous portions at least partially surrounding said central portion.

15. The hood as claimed in claim 14, wherein at least one portion comprises a different plastic material than another portion.

16. The hood as claimed in claim 14, wherein a portion is disposed along a peripheral edge of the hood, is produced from a soft and elastic material, and is designed for sealing against an abutment ring which is disposed along the peripheral edge of the hood and designed to abut against a head of a wearer of the hearing protector in which the hood is included.

17. The hood as claimed in claim 14 wherein one of said at least two contiguous portions comprises a softer plastic than the other of said contiguous portions.

18. The hood as claimed in claim 14 including an abutment ring attached to said hood.

19. A method of producing a hood for a hearing protector, the hood having an outer surface and an inner surface, comprising:
injection molding a first plastic material to form a first portion;
injection molding a second plastic material to form a second portion, said first and second portions being mutually contiguous to each other to define a single contiguous hood, said first and second portions being separated by a separation line which is visible on said outer surface of said hood, said first portion comprising a central portion and said second portion at least partially surrounding said central portion, said first plastic material having different properties in at least one respect from said second plastic material and wherein one of said first or second plastic materials is softer relative to the other of said first or second plastic materials.

20. A hood for a hearing protector produced from plastic injection molding comprising:
a first portion formed from injection molding a first plastic material;
a second portion formed from injection molding a second plastic material;
said first and second portions being mutually contiguous to each other to define a single contiguous hood, said first and second portions being separated by a separation line which is visible on said outer surface of said hood, said first portion comprising a central portion and said second portion at least partially surrounding said central portion, said first plastic material having different properties in at least one respect from said second plastic material and wherein one of said first or second plastic materials is softer relative to the other of said first or second plastic materials.

21. A hood for a hearing protector comprising:
a first portion formed from a first plastic material;
a second portion formed from a second plastic material;
said first and second portions being mutually contiguous to each other to define a single contiguous hood, said first and second portions being separated by a separation line which is visible on said outer surface of said hood, said first portion comprising a central portion and said second portion at least partially surrounding said central portion, said first plastic material having different properties in at least one respect from said second plastic material and wherein one of said first or second plastic materials is softer relative to the other of said first or second plastic materials.

22. A method of producing a hearing protector comprising a hood and an abutment ring, the abutment ring being disposed along a peripheral edge of the hood, the abutment ring intended to abut against the head of a wearer of the hearing protector in which the hood is included, wherein the hood is produced by a method, comprising:
injection molding of plastic material into a single contiguous piece employing plastic materials with different properties in at least one respect.

23. The method as claimed in claim 22, wherein the plastic materials are employed in both homogeneous and in porous or foamed form.

24. The method as claimed in claim 22, wherein at least two different plastic materials are employed.

25. The method as claimed in claim 24, wherein plastic materials of different densities are employed.

26. The method as claimed in claim 24, wherein plastic materials of different hardnesses are employed.

27. The method as claimed in claim 24, wherein plastic materials with different modulus of elasticity are employed.

28. The method as claimed in claim 22 wherein the single contiguous piece includes at least two contiguous portions.

29. The method as claimed in claim 28 wherein the hood has an outer surface and an inner surface and wherein said at least two contiguous portions are visible on said outer surface.

30. The method as claimed in claim 29 wherein a separation line separates said at least two contiguous portions visible on said outer surface.

31. The method as claimed in claim 30 wherein one of said at least two contiguous portions comprise a central portion and another of said at least two contiguous portions at least partially surrounds said central portion.

32. The method as claimed in claim 30 including two of said contiguous portions wherein one of said portions comprises a softer plastic than the other of said contiguous portions.

33. A hearing protector comprising a hood and an abutment ring, the abutment ring being disposed along a peripheral edge of the hood, the abutment ring intended to abut against the head of a wearer of the hearing protector in which the hood is included, wherein the hood is produced from plastic by injection molding, comprising:
at least two mutually contiguous portions which comprise first and second plastic made of different materials and with different properties in at least one respect.

34. The hearing protector as claimed in claim 33, wherein the portions include an outer and an inner layer of a first plastic material with a first group of properties and an intermediate layer located therebetween and comprising a second plastic material with a second group of properties.

35. The hearing protector as claimed in claim 34, wherein the outer and inner layers have a hardness greater than the intermediate layer.

36. The hearing protector as claimed in claim 35, wherein the intermediate layer has a hardness greater than the outer and inner layers.

37. The hearing protector as claimed in claim 33, wherein the portions include two material layers, of which at least one has surfaces which are free towards both an outside and an inside of the hood.

38. The hearing protector as claimed in claim 33, wherein the portions include two material layers which both have surfaces which are free towards an outside of the hood and surfaces which are free towards the inside of the hood.

39. The hearing protector as claimed in claim 33, wherein at least one portion comprises a different plastic material than another portion.

40. The hearing protector as claimed in claim 33 wherein a contiguous portion disposed along said peripheral edge of the hood is produced from a soft and elastic material and is designed for sealing against said abutment ring.

41. The hearing protector as claimed in claim 35, wherein the intermediate layer has a foam structure.

42. The hearing protector as claimed in claim 36, wherein the outer and inner layers have a foam structure.

43. The hearing protector as claimed in claim 33 wherein the hood has an outer surface and an inner surface and wherein said at least two contiguous portions are visible on said outer surface.

44. The hearing protector as claimed in claim 43 wherein a separation line separates said at least two contiguous portions visible on said outer surface.

45. The hearing protector as claimed in claim 44 wherein one of said at least two portions comprise a central portion and another of said at least two portions at least partially surrounds said central portion.

46. The hearing protector as claimed in claim 44 including two of said contiguous portions wherein one of said portions comprises a softer plastic than the other of said contiguous portions.

47. A hearing protector comprising a hood and an abutment ring, the abutment ring being disposed along a peripheral edge of the hood, the abutment ring intended to abut against the head of a wearer of the hearing protector in which the hood is included, wherein the hood comprises:
at least two mutually contiguous portions which comprise first and second plastic made of different materials and with different properties in at least one respect.

48. The hearing protector as claimed in claim 47, wherein the portions include an outer and an inner layer of a first plastic material with a first group of properties and an intermediate layer located therebetween and comprising a second plastic material with a second group of properties.

49. The hearing protector as claimed in claim 48, wherein the outer and inner layers have a hardness greater than the intermediate layer.

50. The hearing protector as claimed in claim 48, wherein the intermediate layer has a hardness greater than the outer and inner layers.

51. The hearing protector as claimed in claim 47, wherein the portions include two material layers, of which at least one has surfaces which are free towards both an outside and an inside of the hood.

52. The hearing protector as claimed in claim 47, wherein the portions include two material layers which both have surfaces which are free towards an outside of the hood and surfaces which are free towards the inside of the hood.

53. The hearing protector as claimed in claim 47, wherein at least one portion comprises a different plastic material than another portion.

54. The hearing protector as claimed in claim 47, wherein a contiguous portion disposed along said peripheral edge of the hood is produced from a soft and elastic material and is designed for sealing against said abutment.

55. The hearing protector as claimed in claim 49, wherein the intermediate layer has a foam structure.

56. The hearing protector as claimed in claim 50, wherein the outer and inner layers have a foam structure.

57. The hearing protector as claimed in claim 47 wherein the hood has an outer surface and an inner surface and wherein said at least two contiguous portions are visible on said outer surface.

58. The hearing protector as claimed in claim 57 wherein a separation line separates said at least two contiguous portions visible on said outer surface.

59. The hearing protector as claimed in claim 58 wherein one of said portions comprise a central portion and another of said portions at least partially surrounds said central portion.

60. The hearing protector as claimed in claim 58 including two of said contiguous portions wherein one of said portions comprises a softer plastic than the other of said contiguous portions.

61. A method of producing a hood intended for use with a hearing protector where the hearing protector comprises a hood and an abutment ring, the abutment ring intended to be disposed along a peripheral edge of the hood, wherein the hood is produced by a method consisting essentially of injection molding of plastic material into a single contiguous piece employing plastic materials with different properties in at least one respect.

62. The method as claimed in claim 61, wherein the plastic materials are employed in both homogeneous and in porous or foamed form.

63. The method as claimed in claim 61, wherein at least two different plastic materials are employed.

64. The method as claimed in claim 63, wherein plastic materials of different densities are employed.

65. The method as claimed in claim 63, wherein plastic materials of different hardnesses are employed.

66. The method as claimed in claim 63, wherein plastic materials with different modulus of elasticity are employed.

67. The method as claimed in claim 61 wherein the single contiguous piece includes at least two contiguous portions.

68. The method as claimed in claim 67 wherein the hood has an outer surface and an inner surface and wherein said at least two contiguous portions are visible on said outer surface.

69. The method as claimed in claim 68 wherein a separation line separates said at least two contiguous portions visible on said outer surface.

70. The method as claimed in claim 69 wherein one of said at least two contiguous portions comprise a central portion and another of said at least two contiguous portions at least partially surrounds said central portion.

71. The method as claimed in claim 69 including two of said contiguous portions wherein one of said portions comprises a softer plastic than the other of said contiguous portions.

72. A hood intended for use with a hearing protector, the hearing protector comprising a hood and an abutment ring, the abutment ring intended to be disposed along a peripheral edge of the hood, wherein the hood is produced from plastic by injection molding, consisting essentially of:
at least two mutually contiguous portions which comprise plastic materials with different properties in at least one respect.

73. The hood as claimed in claim 72, wherein the portions include an outer and an inner layer of a first plastic material with a first group of properties and an intermediate layer located therebetween and comprising a second plastic material with a second group of properties.

74. The hood as claimed in claim 73, wherein the outer and inner layers have a hardness greater than the intermediate layer.

75. The hood as claimed in claim 74, wherein the intermediate layer has a hardness greater than the outer and inner layers.

76. The hood as claimed in claim 72, wherein the portions include two material layers, of which at least one has surfaces which are free towards both an outside and an inside of the hood.

77. The hood as claimed in claim 72, wherein the portions include two material layers which both have surfaces which are free towards an outside of the hood and surfaces which are free towards the inside of the hood.

78. The hood as claimed in claim 72, wherein at least one portion comprises a different plastic material than another portion.

79. The hood as claimed in claim 72 wherein a contiguous portion disposed along said peripheral edge of the hood is produced from a soft and elastic material and is designed for sealing against said abutment ring.

80. The hood as claimed in claim 74, wherein the intermediate layer has a foam structure.

81. The hood as claimed in claim 75, wherein the outer and inner layers have a foam structure.

82. The hood as claimed in claim 72 wherein the hood has an outer surface and an inner surface and wherein said at least two contiguous portions are visible on said outer surface.

83. The hood as claimed in claim 82 wherein a separation line separates said at least two contiguous portions visible on said outer surface.

84. The hood as claimed in claim 83 wherein one of said at least two portions comprise a central portion and another of said at least two portions at least partially surrounds said central portion.

85. The hood as claimed in claim 83 including two of said contiguous portions wherein one of said portions comprises a softer plastic than the other of said contiguous portions.

86. A hood intended for use with a hearing protector, the hearing protector comprising a hood and an abutment ring, the abutment ring intended to be disposed along a peripheral edge of the hood, wherein the hood consists essentially of:
at least two mutually contiguous portions which comprise plastic materials with different properties in at least one respect.

87. The hood as claimed in claim 86, wherein the portions include an outer and an inner layer of a first plastic material with a first group of properties and an intermediate layer located therebetween and comprising a second plastic material with a second group of properties.

88. The hood as claimed in claim 87, wherein the outer and inner layers have a hardness greater than the intermediate layer.

89. The hood as claimed in claim 87, wherein the intermediate layer has a hardness greater than the outer and inner layers.

90. The hood as claimed in claim 86, wherein the portions include two material layers, of which at least one has surfaces which are free towards both an outside and an inside of the hood.

91. The hood as claimed in claim 86, wherein the portions include two material layers which both have surfaces which are free towards an outside of the hood and surfaces which are free towards the inside of the hood.

92. The hood as claimed in claim 86, wherein at least one portion comprises a different plastic material than another portion.

93. The hood as claimed in claim 86, wherein a contiguous portion disposed along said peripheral edge of the hood is produced from a soft and elastic material and is designed for sealing against said abutment.

94. The hood as claimed in claim 88, wherein the intermediate layer has a foam structure.

95. The hood as claimed in claim 89, wherein the outer and inner layers have a foam structure.

96. The hood as claimed in claim 86 wherein the hood has an outer surface and an inner surface and wherein said at least two contiguous portions are visible on said outer surface.

97. The hood as claimed in claim 96 wherein a separation line separates said at least two contiguous portions visible on said outer surface.

98. The hood as claimed in claim 97 wherein one of said portions comprise a central portion and another of said portions at least partially surrounds said central portion.

99. The hood as claimed in claim 97 including two of said contiguous portions wherein one of said portions comprises a softer plastic than the other of said contiguous portions.

100. A method of producing a hood for a hearing protector, comprising:

injection molding the hood from plastic materials to form a single piece having at least two contiguous portions, the plastic materials adhering to one another during the inject molding process, the plastic materials having different properties in at least one respect so as to improve the sound suppression capability of the hood by sound wave interference at an interface between the at least two contiguous portions.

101. The method as claimed in claim 100 wherein the plastic materials are employed in both homogeneous and in porous or foamed form.

102. The method as claimed in claim 100 wherein at least two different plastic materials are employed.

103. The method as claimed in claim 102 wherein plastic materials of different densities are employed.

104. The method as claimed in claim 102 wherein plastic materials of different hardnesses are employed.

105. The method as claimed in claim 102 wherein plastic materials with different modulus of elasticity are employed.

106. A hood for a hearing protector, the hood being produced from plastic by injection molding, wherein the hood includes at least two mutually contiguous portions or layers which consist of plastic materials, the plastic materials adhering to one another during the injection molding cycle, with the plastic materials having different properties in at least one respect so as to improve the sound-suppression capability of the hood by sound wave interference at an interface between the contiguous portions or layers.

107. The hood as claimed in claim 106 wherein the portions include an outer and an inner layer of a plastic material with a first group of properties and an intermediate layer located therebetween, the intermediate layer comprising a plastic material with a second group of properties.

108. The hood as claimed in claim 107 wherein the outer and inner layers are relatively hard, while the intermediate layer is softer or has a foamed structure.

109. The hood as claimed in claim 107 wherein the intermediate layer is relatively hard while the outer and inner layers are softer or have a foamed structure.

110. The hood as claimed in claim 106 wherein the portions include two material layers, of which at least one has surfaces which are exposed to both the outside of the hood and to the inside of the hood.

111. The hood as claimed in claim 106 wherein the portions include two material layers which both have surfaces which are exposed to the outside of the hood and surfaces which are exposed to the inside of the hood.

112. The hood as claimed in claim 106 wherein at least one of the portions or layers comprised a different plastic material than the other portion or layers.

113. The hood as claimed in claim 106 wherein a portion is disposed along the peripheral edge of the hood, wherein such portion is produced from a soft and elastic material and is intended to seal against an abutment ring which is disposed along a peripheral edge of the hood, the abutment ring intended to abut against the head of the wearer of the hearing protector in which the hood is included.

* * * * *